US010420369B2

(12) United States Patent
Wanner

(10) Patent No.: US 10,420,369 B2
(45) Date of Patent: Sep. 24, 2019

(54) EXTINGUISHER PACKAGE FOR A SMOKING ARTICLE

(71) Applicant: Philip Morris Products S.A., Neuchatel (CH)

(72) Inventor: Pierre Wanner, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/526,349

(22) PCT Filed: Nov. 25, 2015

(86) PCT No.: PCT/EP2015/077694
§ 371 (c)(1),
(2) Date: May 12, 2017

(87) PCT Pub. No.: WO2016/083474
PCT Pub. Date: Jun. 2, 2016

(65) Prior Publication Data
US 2017/0325501 A1 Nov. 16, 2017

(30) Foreign Application Priority Data
Nov. 25, 2014 (EP) ..................................... 14194800

(51) Int. Cl.
*A24F 13/18* (2006.01)
*A24F 47/00* (2006.01)
*A61M 15/06* (2006.01)

(52) U.S. Cl.
CPC ............ *A24F 13/18* (2013.01); *A24F 47/006* (2013.01); *A61M 15/06* (2013.01)

(58) Field of Classification Search
CPC ...... A24F 13/18; A24F 13/20; A24F 19/0064; A24F 19/0078; A24F 15/08; A24F 15/18; A24F 13/02; A24F 19/0085; B65D 85/10
(Continued)

(56) References Cited

U.S. PATENT DOCUMENTS 1,846,252 A * 2/1932 Ford ....................... A24F 13/18
131/237
2,051,067 A * 8/1936 Arians .................... A24F 13/18
131/235.1
(Continued)

FOREIGN PATENT DOCUMENTS

CN 87 2 02157 U 6/1988
CN 1039710 A 2/1990
(Continued)

OTHER PUBLICATIONS

International Search Report and Written Opinion dated Feb. 10, 2016 in PCT/EP2015/077694, filed Nov. 25, 2015.
(Continued)

*Primary Examiner* — Steven A. Reynolds
(74) *Attorney, Agent, or Firm* — Oblon, McClelland, Maier & Neustadt, L.L.P.

(57) ABSTRACT

A package for a smoking article is provided, including a base layer and an elongate recess each having first and second ends; a cover layer having first and second ends and overlying the elongate recess, the cover layer and the elongate recess together defining a cavity configured to receive the smoking article. Each of the first end of the elongate recess and the first end of the cover layer includes a thermally insulating portion. A maximum width of the first end of the cavity between the base layer and the cover layer is greater than a corresponding maximum width of the second end of the cavity. The cover layer is moveable between an open position in which the smoking article can be removed from the cavity and reinserted, and a closed position in which the cover layer can substantially seal and extinguish the smoking article within the cavity.

14 Claims, 2 Drawing Sheets

(58) Field of Classification Search
USPC .............. 206/246, 268, 261; 131/235.1, 256, 131/237.5, 237, 231
See application file for complete search history.

(56) References Cited

U.S. PATENT DOCUMENTS

| | | | | |
|---|---|---|---|---|
| 3,601,132 | A | * | 8/1971 | Etheridge ............... A24F 13/18 131/256 |
| 4,886,076 | A | | 12/1989 | Gilbert et al. |
| 5,040,552 | A | | 8/1991 | Schleich et al. |
| 5,377,826 | A | * | 1/1995 | Ayres ...................... A24F 13/18 131/235.1 |
| 5,595,577 | A | | 1/1997 | Bensalem et al. |
| 5,598,854 | A | * | 2/1997 | Gillie ...................... A24F 19/14 131/235.1 |
| 5,996,783 | A | * | 12/1999 | Herchelroth ........ A24F 19/0064 206/245 |
| 6,010,462 | A | | 1/2000 | Stoermer, III |
| 7,409,955 | B2 | * | 8/2008 | Mauldin ................ A24F 13/20 131/233 |
| 2008/0251089 | A1 | | 10/2008 | Granda et al. |
| 2010/0224514 | A1 | | 9/2010 | Urf et al. |
| 2011/0147253 | A1 | * | 6/2011 | Chung ............... A47J 27/21166 206/459.1 |
| 2013/0312775 | A1 | | 11/2013 | Cortesi |
| 2015/0313279 | A1 | | 11/2015 | Lavanchy et al. |
| 2015/0366264 | A1 | * | 12/2015 | Theron .................. A24F 15/08 206/85 |

FOREIGN PATENT DOCUMENTS

| | | |
|---|---|---|
| CN | 2242589 Y | 12/1996 |
| CN | 2390429 Y | 8/2000 |
| CN | 201356061 Y | 12/2009 |
| DE | 3336772 A1 | 10/1984 |
| DE | 20 2005 014 517 U1 | 3/2007 |
| RU | 42 171 U1 | 6/1996 |
| RU | 28 588 U1 | 4/2003 |
| WO | WO 02/00047 A1 | 1/2002 |
| WO | WO 2009/022232 A2 | 2/2009 |
| WO | WO 2009/043072 A1 | 4/2009 |
| WO | WO 2010/025545 A1 | 3/2010 |
| WO | WO 2010/037529 A1 | 4/2010 |
| WO | WO 2012/110948 A1 | 8/2012 |
| WO | WO 2013/104616 A1 | 7/2013 |
| WO | WO 2014/122200 A1 | 8/2014 |
| WO | WO 2015/181379 A2 | 12/2015 |

OTHER PUBLICATIONS

Russian Notice of Allowance with English translation dated Mar. 25, 2019 in corresponding Russian Patent Application No. 2017122132, (13 pages).

Chinese Office Action dated Jun. 28, 2019 in Chinese Application No. 201580061978.1 (with English Translation), 16 pages.

* cited by examiner

EXTINGUISHER PACKAGE FOR A SMOKING ARTICLE

The present invention relates to a package for a smoking article, wherein the package also functions as an extinguisher for the smoking article. The present invention also relates to a packaged smoking article comprising a smoking article having a combustible heat source and contained within the package according to the present invention.

A number of smoking articles in which tobacco is heated rather than combusted have been proposed in the art. An aim of such 'heated' smoking articles is to reduce known harmful smoke constituents of the type produced by the combustion and pyrolytic degradation of tobacco in conventional cigarettes. In one known type of heated smoking article, an aerosol is generated by the transfer of heat from a combustible heat source to a physically separate aerosol-forming substrate, such as tobacco. The aerosol-forming substrate may be located within, around or downstream of the combustible heat source. For example, WO-A2-2009/022232 discloses a smoking article comprising a combustible heat source, an aerosol-forming substrate downstream of the combustible heat source, and a heat-conducting element around and in contact with a rear portion of the combustible heat source and an adjacent front portion of the aerosol-forming substrate. During smoking, volatile compounds are released from the aerosol-forming substrate by heat transfer from the combustible heat source and entrained in air drawn through the smoking article. As the released compounds cool, they condense to form an aerosol that is inhaled by the user.

Smoking articles which include a combustible fuel element or heat source may have a combustion zone or zone of heating that is larger, more dense, and not as readily extinguished by crushing or "stubbing out" the heat source compared to a conventional cigarette, in which tobacco is burnt or combusted to heat and release volatile compounds from the tobacco. Such smoking articles may have a heat source that contains significantly more energy in the form of heat than found in the combustion zone of a conventional cigarette. Consequently, such smoking articles may require more effort to extinguish or to remove sufficient heat to facilitate disposal.

It would be desirable to provide an improved extinguisher for smoking articles, particularly one which may be used with smoking articles that include a combustible fuel element or heat source. In particular, it would be desirable to provide an extinguisher which is both simple to manufacture and convenient to use. In addition, it would be desirable to provide an extinguisher which can be readily kept unobtrusively together with the smoking article so as to avoid the need of having a separate element to extinguish the smoking article after use.

According to a first aspect of the present invention, there is provided a package for a smoking article, the package comprising a base layer having first and second ends and comprising an elongate recess for receiving a smoking article, the elongate recess having first and second ends. The package further comprises a cover layer having first and second ends and overlying the elongate recess so that the cover layer and the elongate recess together define a cavity for receiving a smoking article, the cavity having first and second ends. Each of the first end of the elongate recess and the first end of the cover layer comprises a thermally insulating portion, and the maximum width of the first end of the cavity between the base layer and the cover layer is greater than the maximum width of the second end of the cavity between the base layer and the cover layer. The cover layer is moveable between an open position in which a smoking article can be removed from the cavity and reinserted into the cavity, and a closed position in which the cover layer can substantially seal a smoking article within the cavity to extinguish the smoking article after the smoking article has been ignited.

According to a second aspect of the present invention, there is provided a package for a smoking article, the package comprising a base layer having first and second ends and comprising an elongate recess for receiving a smoking article, the elongate recess having first and second ends. The package further comprises a cover layer having first and second ends and overlying the elongate recess so that the cover layer and the elongate recess together define a cavity for receiving a smoking article, the cavity having first and second ends. Each of the first end of the elongate recess and the first end of the cover layer comprises a thermally insulating portion, and the cover layer is moveable between an open position in which a smoking article can be removed from the cavity and reinserted into the cavity, and a closed position in which the cover layer can substantially seal a smoking article within the cavity to extinguish the smoking article after the smoking article has been ignited.

Providing a package for a smoking article that can be reclosed around the smoking article after the smoking article has been smoked advantageously eliminates the need for a separate extinguisher. That is, the package functions both as a package to protect the smoking article and to maintain freshness prior to smoking of the smoking article, and an extinguisher to extinguish the combustible heat source after the smoking article has been smoked. Therefore, a package for a smoking article according to the present invention provides a convenient way for a consumer to extinguish a smoking article without the need to carry a separate extinguisher.

Furthermore, the thermally insulating portions of the elongate recess and the cover layer advantageously reduce the transfer of heat from a smoking article to the exterior of the package when the smoking article is extinguished.

In some embodiments, the first end of at least one of the base layer and the cover layer is shaped so that the first end is spaced apart from a smoking article when the smoking article is received within the cavity and the cover layer is in the closed position, and wherein the thermally insulating portion comprises the spaced apart portion.

In preferred embodiments, the first ends of both the base layer and the cover layer are shaped so that the first ends are spaced apart from a smoking article when the smoking article is received within the cavity and the cover layer is in the closed position. Each thermally insulating portion comprises the respective spaced apart portion.

In those embodiments comprising one or more spaced apart portions, the spaced apart portions advantageously space one or both of the base layer and the cover layer away from a first end of a smoking article during extinguishing of the smoking article, therefore reducing the transfer of heat from the smoking article to the exterior of the package.

In any of the embodiments described above, at least one of the base layer and the cover layer comprises an inner wall and an outer wall spaced from the inner wall to create an insulating gap, wherein the insulating portion comprises the insulating gap. Preferably, both the base layer and the cover layer each comprise an inner wall and an outer wall spaced from the inner wall to create an insulating gap, wherein each insulating portion comprises the respective insulating gap.

Utilising inner and outer walls to create an insulating gap in one or both of the base layer and the cover layer advantageously further reduces the transfer of heat from a smoking article to the exterior of the package during extinguishing of the smoking article.

In those embodiments in which one or both of the base layer and the cover layer comprises an inner wall and an outer wall, the inner wall is preferably formed from a material having a melting temperature above the combustion temperature of the smoking article. For example, the inner wall may be formed from a metal foil, such as a foil of aluminium or an aluminium alloy.

Additionally, or alternatively, the outer wall is preferably formed from a thermally insulating material to minimise the transfer of heat from a smoking article to the exterior of the package during extinguishing of the smoking article. For example, the outer wall may be formed from a polymeric material, such as polypropylene, polyphenylene sulphide, poly(vinyl chloride), polyvinylidene chloride, polyethylene terephthalate, polyethersulfone, and polyetherimide.

In those embodiments in which at least one of the base layer and the cover layer comprises an insulating gap, the insulating gap may be at least partially filled with air. Additionally, or alternatively, the insulating gap may be at least partially filled with a solid insulating material. For example, suitable solid insulating materials may include at least one of a glass, a metal, a metal oxide, a ceramic, a polymeric material, a stone material, and combinations thereof. Particularly suitable materials include woven and non-woven glass fibre materials, basalt fibres, pumice, and aramid polymers. Further suitable insulating materials include those listed under Class-C in the JIS C 4003 standards (insulating materials rated to withstand temperatures of 180 degrees Celsius or higher), including at least one of mica, ceramic, glass, quartz, polytetrafluoroethylene resins, varnish glass cloth adhered, impregnated or coated with silicone resin, and combinations thereof. Additionally, or alternatively, the solid insulating material may comprise at least one of calcium silicate, cellular glass, cellular aramid, vermiculite, fibreglass, moulded or extruded compounds of polyetrafluoroethylene resins with fiberglass, and mineral stone.

Additionally, or alternatively, a solid insulating material may be provided on an inner surface of the insulating portion of one or both of the elongate recess and the cover layer. Suitable solid insulating materials include those listed above with respect to solid insulating materials that may be provided in an insulating gap. In particular, suitable solid insulating materials may include at least one of a glass, a metal, a metal oxide, a ceramic, a polymeric material, a stone material, and combinations thereof. Particularly suitable materials include woven and non-woven glass fibre materials, basalt fibres, pumice, and aramid polymers. Further suitable insulating materials include those listed under Class-C in the JIS C 4003 standards (insulating materials rated to withstand temperatures of 180 degrees Celsius or higher), including at least one of mica, ceramic, glass, quartz, polytetrafluoroethylene resins, varnish glass cloth adhered, impregnated or coated with silicone resin, and combinations thereof. Additionally, or alternatively, the solid insulating material may comprise at least one of calcium silicate, cellular glass, cellular aramid, vermiculite, fibreglass, moulded or extruded compounds of polyetrafluoroethylene resins with fiberglass, and mineral stone.

In some embodiments, the solid insulating material may comprise a heat-reflective material which advantageously reflects heat radiating from the smoking article during extinguishing of the smoking article. As used herein the term 'heat reflective material' refers to a material that has a relatively high heat reflectivity and a relatively low heat emissivity such that the material reflects a greater proportion of incident radiation from its surface than it emits. Preferably, the material reflects more than 50% of incident radiation, more preferably more than 70% of incident radiation and most preferably more than 75% of incident radiation.

In any of the embodiments described above, a thermally sensitive ink may be provided on an outer surface of at least one of the base layer and the cover layer to provide an indication of the temperature of the package during extinguishing of a smoking article. For example, the thermally sensitive ink may be configured to change colour when a lit smoking article is inserted into the package to indicate that the package is hot. Additionally, or alternatively, the thermally sensitive ink may be printed in the form of indicia to further improve the warning to the consumer that the smoking article is at an elevated temperature. Additionally, or alternatively, the thermally sensitive ink may be configured to indicate when the package has cooled to a safe temperature after the extinguishing of the smoking article to indicate that the package is safe to handle and it is safe to dispose the smoking article.

In any of the embodiments described above, the cover layer may comprise a flexible sheet material sealed to the base layer around the periphery of the elongate recess. In such embodiments, the cover layer can be peeled away from the base layer to allow removal of a smoking article from the package. Similarly, the flexible cover layer can be rolled or otherwise laid back across the base layer to re-cover the elongate recess to extinguish a lit smoking article when reinserted into the package. To prevent complete detachment of the cover layer from the base layer, preferably a portion of the cover layer is permanently attached to a portion of the base layer at a periphery of the elongate recess. For example, the cover layer may be thermally bonded to the base layer, or the cover layer may be attached to the base layer using a permanent adhesive.

To help re-seal the cover layer to the base layer to facilitate the extinguishing of the smoking article, the package may further comprise a resealable adhesive between the base layer and the flexible cover layer and extending around at least a portion of the periphery of the elongate recess.

The resealable adhesive is preferably applied as a layer having a thickness of between about 0.1 millimeters to about 1 millimeter, preferably between about 0.2 millimeters and about 0.5 millimeters.

As an alternative to a resealable adhesive, the package may comprise two compatible sealing layers that form a seal when brought into contact with each other. Suitable seals include combinations of at least one non-polar polymer layer with at least one polar polymer layer. Suitable non-polar polymers include polyethylene, metallocene polyethylene, and polypropylene. Suitable polar polymers include ethylene-vinyl acetate, an acid copolymer, and an ionomer.

The sealing layers preferably have a combined thickness of between about 0.1 millimeters to about 1 millimeter, preferably between about 0.2 millimeters and about 0.5 millimeters.

In addition to a resealable adhesive or sealing layers that provide a reseal mechanism between the cover layer and the base layer, the package may also comprise a breakable, non-resealable seal between the flexible cover layer and the base layer. For example, a portion of the cover layer may be heat-sealed to a portion of the base layer, wherein the heat seal is broken upon the consumer opening the package for the first time. Such a seal may reduce the risk of accidental opening of the package and may also provide tamper evidence to reassure the consumer that the package has not been opened previously.

In those embodiments in which the cover layer is formed from a flexible sheet material, the package may form part of a 'blister pack' of packages for smoking articles. For example, the base layer may comprise multiple elongate recesses each configured to receive a smoking article and a cover layer may cover each elongate recess. In such embodiments, each cover layer can be formed separately, or the cover layers may be formed from a single piece of material and delineated by frangible portions, such as perforation lines, to allow each elongate recess to be uncovered individually.

In those embodiments in which the package forms part of a blister pack of packages for smoking articles, only one of the 'blisters' may comprise a cavity defined between an elongate recess and a cover layer having the features according to the present invention. That is, only one of the 'blisters' in the blister pack may function as a cavity for extinguishing smoking articles. In such embodiments, the consumer preferably smokes a smoking article contained within the extinguisher cavity first, so that the smoking article within that cavity can be extinguished and discarded. The extinguishing cavity is then free for use in extinguishing subsequent smoking articles from the remaining blisters as they are smoked by the consumer.

Alternatively, each of the 'blisters' may function as a package for a smoking article, according to the present invention in accordance with any of the embodiments described above, so that each cavity can be used to extinguish a smoking article after it has been smoked. In such embodiments, the base layer preferably comprises a frangible portion, such as a perforation line, between consecutive elongate recesses so that each package can be removed from the blister pack and discarded after it has been used to extinguish a smoking article.

As an alternative to those embodiments in which the cover layer is formed from a flexible sheet material, the cover layer may depend from the base layer along a hinge line. For example, a single sheet of material may be folded along a fold line to form a cover layer and a base layer, wherein the fold line forms the hinge line. In such embodiments, the sheet of material is preferably formed from a rigid material, such as a thermoplastic material. For example, a sheet of thermoplastic material may be thermoformed to create the elongate recess. In those embodiments comprising inner and outer walls, the material forming the inner walls and any intervening materials may then be applied to the thermoformed material. The thermoformed material can then be folded so that the first end and the insulating portion of the cover layer overlies the first end and the insulating portion of the base layer. A portion of the cover layer may then be heat sealed to a portion of the base layer to provide a non-resealable seal that must be broken by the consumer upon first opening the package. For resealing the package after the heat seal has been broken, a suitable interference fit may be provided between a portion of the cover layer and a portion of the base layer. For example, after the thermoplastic material has been folded to form the cover layer and the base layer, the thermoplastic material may be further thermoformed to create a 'socket and button' arrangement in which the button is retained in the socket by an interference fit to maintain the cover layer in the closed position after the heat seal has been broken. Additionally, or alternatively, a resealable adhesive or one or more sealing layers may be provided between the cover layer and the base layer, as described above.

In any of the embodiments described above, the package may comprise a material configured to reduce the emission of undesirable odours from a smoking article when the smoked smoking article is inserted into the package. For example, the package may reduce the emission of odours by comprising a material which absorbs or adsorbs the odours. Alternatively, or in addition, the package may comprise a heat-released flavour compound. The flavour compound may be a nanoparticle formed from a low melting point wax encapsulating the flavour compound. The flavour compound is preferably volatile such that it is released into the atmosphere on activation of the nanoparticle.

The present invention also extends to a smoking article packaged in a package as described above. Therefore, according to a third aspect of the present invention there is provided a packaged smoking article, wherein the smoking article comprises a combustible heat source positioned at a first end of the smoking article, an aerosol-forming substrate, and a mouthpiece downstream of the aerosol-forming substrate and positioned at a second end of the smoking article. The smoking article is received within the cavity of a package in accordance with the first or second aspect of the present invention, in accordance with any of the embodiments described above. The thermally insulating portions are positioned adjacent the combustible heat source when the first end of the smoking article is received within the first end of the cavity, and the cover layer is moveable between the open position in which the smoking article can be removed from the cavity and reinserted into the cavity and the closed position in which the cover layer substantially seals the smoking article within the cavity to extinguish the combustible heat source after the combustible heat source has been ignited.

The combustible heat source is preferably a solid heat source, and may comprise any suitable combustible fuel including, but not limited to, carbon and carbon-based materials containing aluminium, magnesium, one or more carbides, one or more nitrides and combinations thereof. Solid combustible heat sources for heated smoking articles and methods for producing such heat sources are known in the art and described in, for example, U.S. Pat. Nos. 5,040,552 and 5,595,577. Typically, known solid combustible heat sources for heated smoking articles are carbon-based, that is they comprise carbon as a primary combustible material.

The combustible heat source is preferably a blind combustible heat source. As used herein, the term 'blind' describes a heat source that does not comprise any air flow channels.

To maximise heat transfer from the combustible heat source to the aerosol-forming substrate the combustible heat source preferably is in close proximity to the aerosol-forming substrate. For example, the aerosol-forming substrate may be positioned immediately downstream from the combustible heat source. Alternatively, the combustible heat source may be substantially annular in shape and may coaxially surround the aerosol-forming substrate.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds, which are released from the substrate upon heating. Alternatively, the aerosol-forming substrate may comprise a non-tobacco material. The aerosol-forming substrate may further comprise one or more aerosol formers. Examples of suitable aerosol formers include, but are not limited to, glycerine and propylene glycol.

In some embodiments, the aerosol-forming substrate is a rod comprising a tobacco-containing material.

If the aerosol-forming substrate is a solid aerosol-forming substrate, the solid aerosol-forming substrate may comprise, for example, one or more of: powder, granules, pellets, shreds, spaghetti strands, strips or sheets containing one or more of: herb leaf, tobacco leaf, fragments of tobacco ribs, reconstituted tobacco, homogenised tobacco, extruded tobacco and expanded tobacco. The solid aerosol-forming substrate may be in loose form, or may be provided in a suitable container or cartridge. For example, the aerosol-forming material of the solid aerosol-forming substrate may be contained within a paper or other wrapper and have the form of a plug. Where an aerosol-forming substrate is in the form of a plug, the entire plug including any wrapper is considered to be the aerosol-forming substrate.

Optionally, the solid aerosol-forming substrate may contain additional tobacco or non-tobacco volatile flavour compounds, to be released upon heating of the solid aerosol-forming substrate. The solid aerosol-forming substrate may also contain capsules that, for example, include the additional tobacco or non-tobacco volatile flavour compounds and such capsules may melt during heating of the solid aerosol-forming substrate.

Optionally, the solid aerosol-forming substrate may be provided on or embedded in a thermally stable carrier. The carrier may take the form of powder, granules, pellets, shreds, spaghetti strands, strips or sheets. The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

The smoking article may comprise a transfer section or transfer element. Such an element may take the form of a hollow tube that is located downstream of the aerosol-forming substrate.

The terms "upstream" and "downstream" as used herein refer to relative positions along the smoking article defined with reference to the direction in which air is drawn through the smoking article by a user. Thus, the mouth end is downstream from the distal end.

Elements forming the smoking article are preferably assembled by means of a suitable wrapper, for example a cigarette paper. A cigarette paper may be any suitable material for wrapping components of a smoking article in the form of a rod. The cigarette paper needs to grip the component elements of the smoking article when the article is assembled and hold them in position within the rod. Suitable materials are well known in the art.

The smoking article may be substantially cylindrical in shape. The smoking article may be substantially elongate. The smoking article has a length and a circumference substantially perpendicular to the length.

The aerosol-forming substrate may be substantially cylindrical in shape. The aerosol-forming substrate may be substantially elongate. The aerosol-forming substrate also has a length and a circumference substantially perpendicular to the length. The aerosol-forming substrate may be located in the smoking article such that the length of the aerosol-forming substrate is substantially parallel to the airflow direction in the smoking article.

In those embodiments in which the smoking article further comprises a transfer section or element, the transfer section or element may be substantially elongate.

The smoking article may have any desired length. For example, the smoking article may have a total length of between approximately 65 mm and approximately 100 mm.

The smoking article may have any desired external diameter. For example, the smoking article may have an external diameter of between approximately 5 mm and approximately 12 mm.

The mouthpiece may comprise a filter. For example, the mouthpiece may comprise a filter plug having one or more segments. Where the mouthpiece comprises a filter plug, preferably the filter plug is a single segment filter plug. The filter plug may comprise one or more segments comprising cellulose acetate, paper or other suitable known filtration materials, or combinations thereof. Preferably, the filter plug comprises filtration material of low filtration efficiency.

The smoking article may be circumscribed by an outer wrapper of, for example, cigarette paper, which has low air permeability. Alternatively or in addition, the mouthpiece may be circumscribed by tipping paper.

The invention will be further described, by way of example only, with reference to the accompanying drawings in which.

Figure 1:
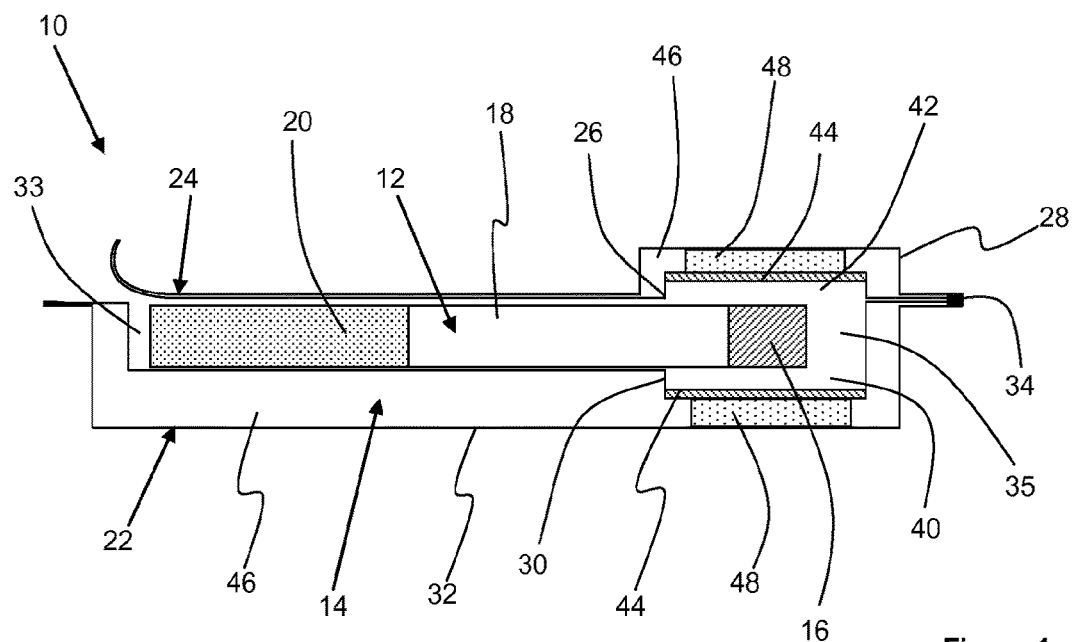
FIG. 1 shows a cross-sectional view of a packaged smoking article in accordance with a first embodiment of the present invention.

FIG. 1 shows a packaged smoking article 10 according to a first embodiment of the present invention, the packaged smoking article 10 comprising a smoking article 12 received within a package 14.

The smoking article 10 comprises a combustible heat source 16 in the form of a carbon block at a first end of the smoking article 12. An aerosol-forming substrate 18 comprising tobacco is positioned downstream of the combustible heat source 16, and a mouthpiece 20 is positioned at a second end of the smoking article 12 downstream of the aerosol-forming substrate 18. In use, the combustible heat source 16 is ignited and heat from the combustible heat source 16 is transferred to the aerosol-forming substrate 18.

The package 14 comprises a base layer 22 and a cover layer 24 overlying the base layer 22. The cover layer 24 is formed from a flexible sheet material comprising an inner wall 26 formed from an aluminium foil and an outer wall 28 formed from a polymeric material. The base layer 22 also comprises an inner wall 30 formed from an aluminium foil and an outer wall 32 formed from a polymeric material. The inner wall 30 is shaped to form an elongate recess 33, the cover layer 24 and the elongate recess 33 together forming a cavity 35 in which the smoking article 12 is received.

A resealable adhesive extends around at least a portion of the periphery of at least one of the base layer 22 and the cover layer 24 so that package can be opened and reclosed by peeling the cover layer 24 away from or back towards the base layer 22. The inner and outer walls of the base layer 22 and the cover layer 24 are secured together with a heat seal 34 at a first end of the package 14 to prevent complete detachment of the cover layer 24 from the base layer 22.

To use the packaged smoking article 10 shown in FIG. 1, a consumer peels open the cover layer 24, removes the smoking article 12 from the package 14 and ignites the combustible heat source 16. After smoking the smoking article 12, the consumer reinserts the smoking article 12 into the package 14 and recloses the cover layer 24. The resealable adhesive substantially seals the cover layer 24 to the base layer 22 so that the smoked smoking article 12 is substantially sealed within the package 14. Once sealed within the package 14, the ignited combustible heat source 16 depletes the oxygen within the elongate recess 33 so that the combustible heat source 16 self-extinguishes.

To reduce the transfer of heat from the combustible heat source 16 to the exterior of the package 14 during extinguishing of the smoking article 12, the base layer 22 and the cover layer 24 comprise insulating portions 40 and 42 comprising portions of the inner surfaces of the base layer 22 and the cover layer 24 that are spaced apart from the combustible heat source 16. That is, a maximum width of a first end of the cavity 35 between the base layer 22 and the cover layer 24 is greater than a maximum width of a second end of the cavity 35 between the base layer 22 and the cover layer 24. The insulating portions 40 and 42 further comprise a solid insulating material 44 comprising basalt fibres provided on the inner surface of each of the base layer 22 and the cover layer 24 to insulate them from the combustible heat source 16.

To further reduce the transfer of heat from the combustible heat source 16 to the exterior of the package 14 during extinguishing of the smoking article 12, the inner and outer walls of the base layer 22 and the cover layer 24 are spaced apart to form insulating gaps 46. The insulating portions 40 and 42 further comprise a solid insulating material 48 provided within each insulating gap 46 adjacent the combustible heat source 16. The remainder of each insulating gap 46 is filled with air.

Figure 2:
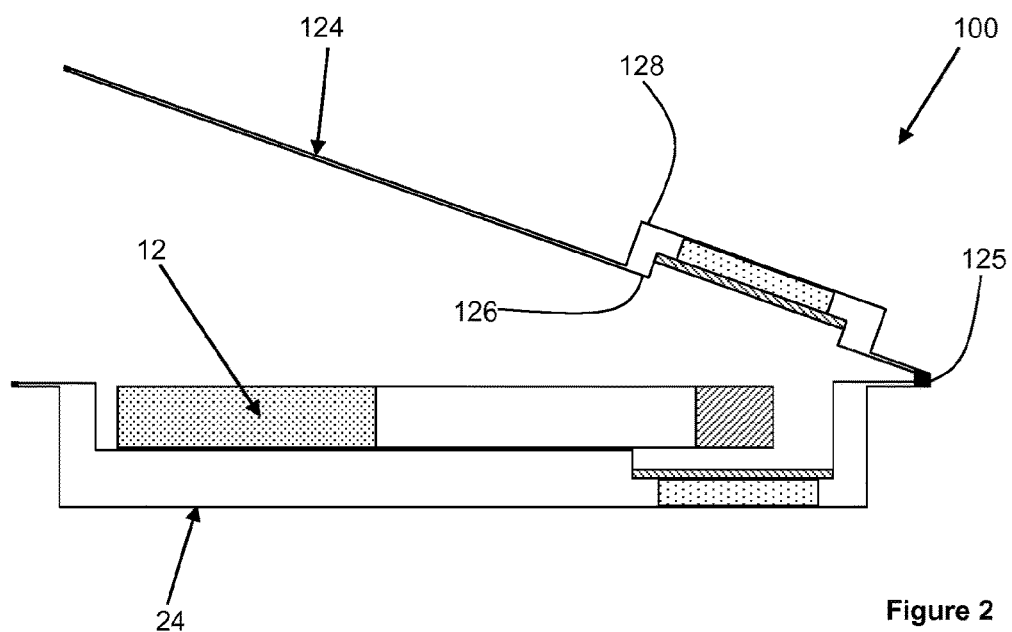
FIG. 2 shows a cross-sectional view of a packaged smoking article in accordance with a second embodiment of the present invention.

FIG. 2 shows a packaged smoking article 100 in accordance with a second embodiment of the present invention. The packaged smoking article 100 shown in FIG. 2 is substantially the same as the packaged smoking article 10 shown in FIG. 1 and like reference numerals designate like parts. The difference between the two packaged smoking articles is the cover layer 124 of the packaged smoking article 100 shown in FIG. 2. Specifically, whereas the cover layer 24 shown in FIG. 1 is formed from a flexible material, the cover layer 124 shown in FIG. 2 is substantially rigid and comprises an inner wall 126 formed from a rigid thermoplastic material laminated with an aluminium foil, and an outer wall 128 formed from a rigid thermoplastic material. Preferably, the outer walls of the base layer 22 and the cover layer 124 are formed from a single sheet of rigid thermoplastic material, wherein a fold line 125 in the thermoplastic material forms a hinge between the base layer 22 and the cover layer 124. After opening the packaged smoking article 100, the cover layer 124 may be reclosed and sealed in the closed position using a resealable adhesive. Alternatively, an interference fit between a portion of the cover layer 124 and a portion of the base layer 22 may retain the cover layer 124 in the closed position.

Figure 3:
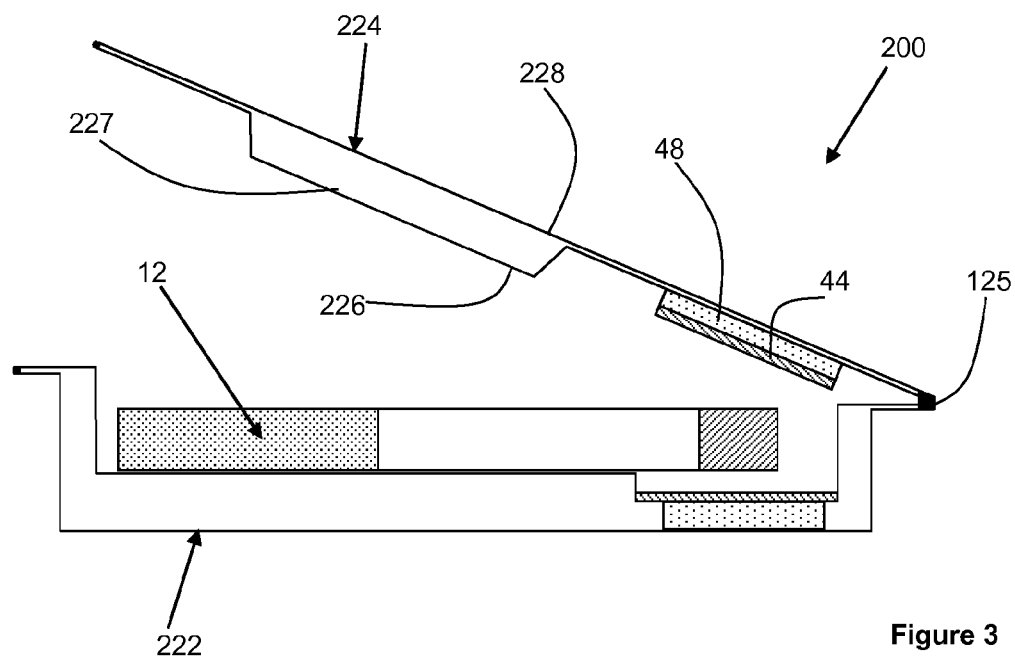
FIG. 3 shows a cross-sectional view of a packaged smoking article in accordance with a third embodiment of the present invention.

FIG. 3 shows a packaged smoking article 200 in accordance with a third embodiment of the present invention. The packaged smoking article 200 shown in FIG. 3 is substantially the same as the packaged smoking article 100 described with reference to FIG. 2, except for the cover layer 224. Specifically, the inner and outer walls 226, 228 of the cover layer 224 are substantially parallel in the region of the insulating portion 42 and the solid insulating material 48 is provided on an inner surface of the inner wall 226 rather than in an insulating gap between the inner and outer walls 226, 228. To ensure that the solid insulating material 44 provided on the cover layer 224 remains spaced apart from the combustible fuel source 16 when the cover layer 224 is in the closed position the base layer 222 forms a deeper elongate recess and the inner wall 226 of the cover layer 224 comprises an elongate protrusion 227 to keep the smoking article 12 in contact with the base layer 222.

Figure 4:
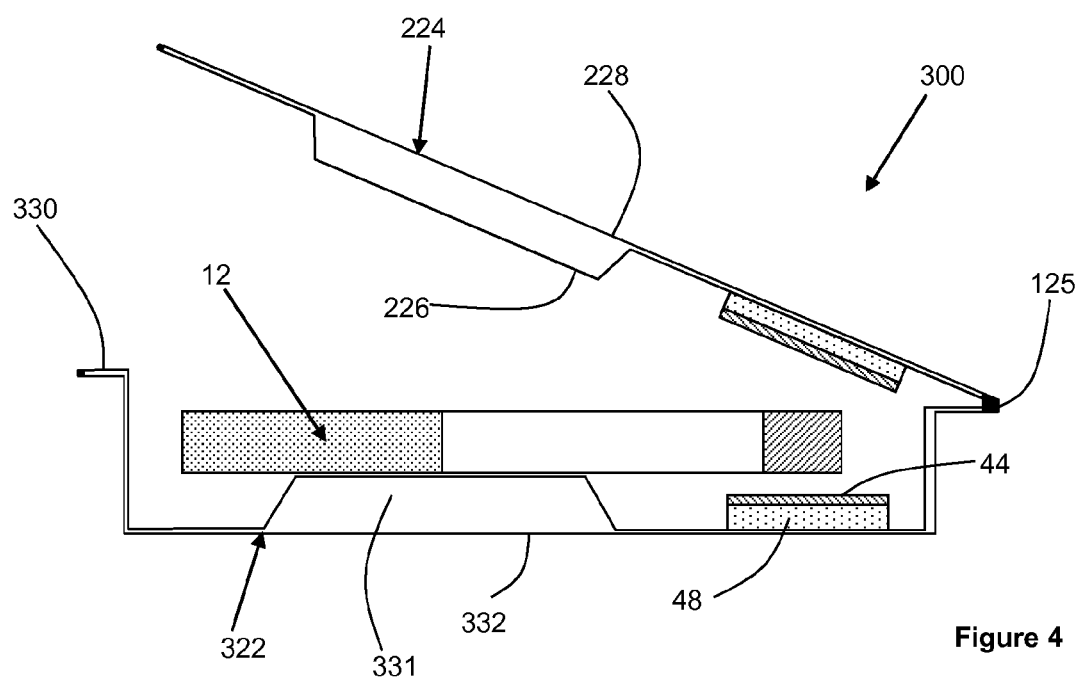
FIG. 4 shows a cross-sectional view of a packaged smoking article in accordance with a fourth embodiment of the present invention.

FIG. 4 shows a packaged smoking article 300 in accordance with a fourth embodiment of the present invention. The packaged smoking article 300 shown in FIG. 4 is substantially the same as the packaged smoking article 200 described with reference to FIG. 3, except for the base layer 322. Specifically, in the same manner as the cover layer 224, the inner and outer walls 330, 332 of the base layer 322 are substantially parallel in the region of the insulating portion 40 and the solid insulating material 48 is provided on an inner surface of the inner wall 330 rather than in an insulating gap between the inner and outer walls 330, 332. To ensure that the solid insulating material 44 provided on the base layer 322 remains spaced apart from the combustible fuel source 16 when the smoking article 12 is received within the cavity the inner wall 330 of the base layer 322 comprises an elongate protrusion 331 to support the smoking article 12.

The invention claimed is:

1. A package for a smoking article, comprising:
    a base layer having first and second ends and comprising an elongate recess configured to receive the smoking article, the elongate recess having first and second ends; and
    a cover layer having first and second ends and overlying the elongate recess so that the cover layer and the elongate recess together define a cavity configured to receive the smoking article, the cavity having first and second ends,
    wherein each of the first end of the elongate recess and the first end of the cover layer comprises a thermally insulating portion,
    wherein a maximum width of the first end of the cavity between a surface of the base layer and a surface of the cover layer is greater than a maximum width of the second end of the cavity between the surface of the base layer and the surface of the cover layer,
    wherein the cover layer is moveable between an open position in which a smoking article can be removed from the cavity and reinserted into the cavity, and a closed position in which the cover layer can substantially seal a smoking article within the cavity to extinguish the smoking article after the smoking article has been ignited
    wherein the first end of at least one of the base layer and the cover layer is shaped so that the first end is spaced apart from the smoking article to define a spaced apart portion when the smoking article is received within the cavity and the cover layer is in the closed position, and
    wherein the thermally insulating portion comprises the spaced apart portion.

2. The package according to claim 1,
    wherein at least one of the base layer and the cover layer comprises an inner wall and an outer wall spaced from the inner wall at the first end to create an insulating gap, and wherein the thermally insulating portion comprises the insulating gap.

3. The package according to claim 2, wherein the inner wall is formed from a metal foil.

4. The package according to claim 2, wherein the outer wall is formed from a polymeric material.

5. The package according to claim 2, wherein the insulating gap is at least partially filled with air.

6. The package according to claim 2, wherein the insulating gap is at least partially filled with a solid insulating material.

7. The package according to claim 1, wherein a solid insulating material is provided on an inner surface at the first end of at least one of the elongate recess and the cover layer.

8. The package according to claim 6, wherein the solid insulating material comprises at least one of a woven material, a non-woven fibrous material, and a porous matrix material.

9. The package according to claim 6, wherein the solid insulating material comprises at least one of a glass, a metal, a metal oxide, a ceramic, a polymeric material, a stone material, and combinations thereof.

10. The package according to claim 1, further comprising a thermally sensitive ink provided on an outer surface of at least one of the base layer and the cover layer.

11. The package according to claim 1, wherein the cover layer comprises a flexible material, the package further comprising a resealable adhesive between the base layer and the cover layer and extending around at least a portion of a periphery of the elongate recess.

12. The package according to claim 1, wherein the cover layer depends from the base layer along a hinge line.

13. A packaged smoking article, comprising:
   a smoking article comprising:
      a combustible heat source disposed at a first end of the smoking article,
      an aerosol-forming substrate, and
      a mouthpiece downstream of the aerosol-forming substrate and disposed at a second end of the smoking article; and
   a package according to claim 1,
      the smoking article being received within the cavity,
      the thermally insulating portions being disposed adjacent the combustible heat source when the first end of the smoking article is received within the first end of the cavity, and
      the cover layer being moveable between the open position in which the smoking article can be removed from the cavity and reinserted into the cavity, and the closed position in which the cover layer substantially seals the smoking article within the cavity to extinguish the combustible heat source after the combustible heat source has been ignited.

14. The packaged smoking article according to claim 13, further comprising a frangible seal sealing the cover layer to the base layer around at least a portion of the periphery of the elongate recess.

* * * * *